_United States Patent_ [19] [11] Patent Number: 5,860,988
Rawlings [45] Date of Patent: Jan. 19, 1999

[54] CIRCUMCISION DEVICE

[76] Inventor: Lawrence Churchill Rawlings, P.O. Box 6287 Charotte Amalie, St Thomas, Virgin Islands (U.S.), 00803

[21] Appl. No.: 808,076

[22] Filed: Feb. 28, 1997

[51] Int. Cl.[6] .................................................. A61B 17/00
[52] U.S. Cl. ............................................................. 606/118
[58] Field of Search ................................... 606/118, 152, 606/153

[56] References Cited

U.S. PATENT DOCUMENTS

| 2,561,176 | 7/1951 | Buckingham | 606/118 |
| 3,612,057 | 10/1971 | Freedman | 606/118 |
| 5,269,788 | 12/1993 | Nelson, III | 606/118 |

FOREIGN PATENT DOCUMENTS 093020766  10/1993  WIPO .

Primary Examiner—William Lewis
Attorney, Agent, or Firm—Nigel L. Scott

[57] ABSTRACT

A device for performing circumcisions comprising two interlockable rings, a larger outer ring which has a continuous groove or channel within its circumference, and a smaller inner ring which has a solid circumference and is sized to fit into the groove or channel of the outer ring so that the two rings can be brought together on the penis during circumcision to form a locking device which clamps the foreskin of the penis into a fixed position inside the groove or channel of the larger outer ring thereby to facilitate the surgical removal of the excess foreskin from the penis by the surgeon.

13 Claims, 4 Drawing Sheets

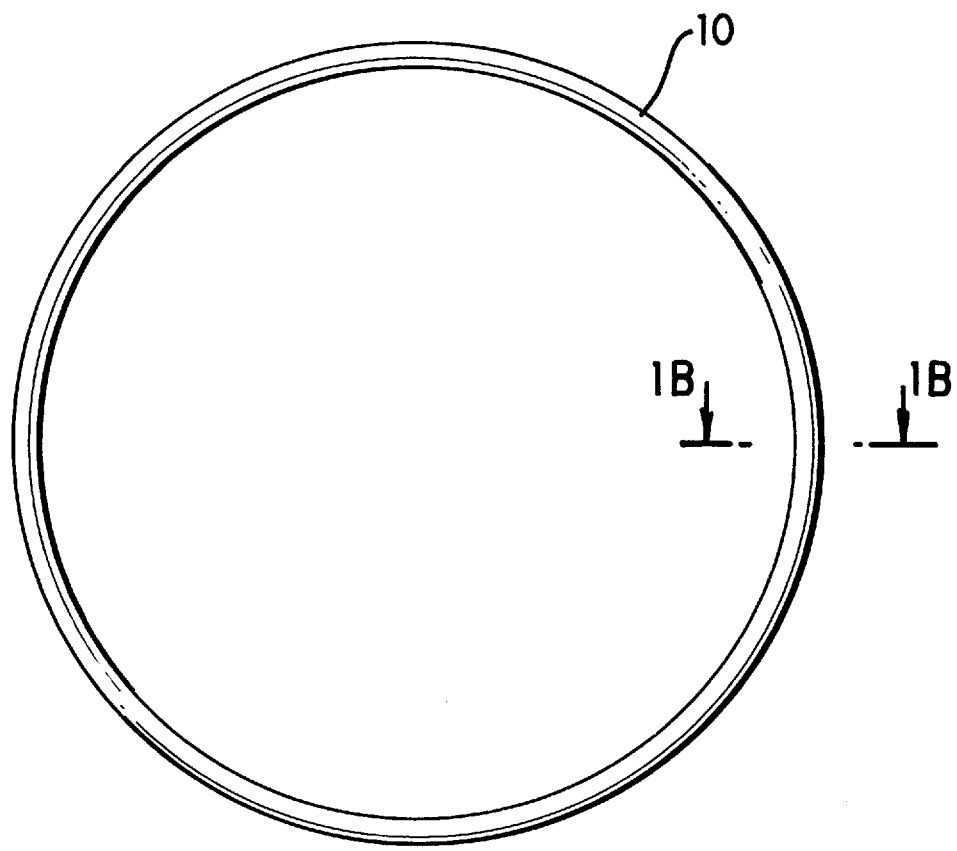

CIRCUMCISION DEVICE

BACKGROUND OF THE INVENTION

This invention relates to an improved surgical device and procedure for performing circumcisions. More particularly, the invention relates to the use of the device as a means of facilitating the removal of excess foreskin from the penis during circumcision. The device is comprised of a pair of rings which are constructed in a manner which permits the smaller ring to be fit into and be locked into the larger ring. When interlocked in this position, the smaller ring clamps the foreskin of the penis in a fixed position so that the penis can be readily circumcised. Both of these rings are made of a material which is absorbable into the body so that after the surgeon performs the circumcission, the rings remain in place on the penis and they are gradually absorbed into the body.

Circumcision, the surgical procedure by which excess foreskin is removed from the penis, is an ancient surgical procedure which is widely known and practiced throughout the world. In some countries, circumcision is a mandatory act connected with the practice of religion in the society; in other societies, young males must be circumcised and experience the trauma and pain associated with circumcision in order to complete the rite of passage into manhood and full acceptance as members of the society. Generally, most circumcisions are performed as a result of a doctor's requirement that a patient have the foreskin of the penis removed for medical or health reasons.

Because of the widespread use and practice of circumcision, a variety of instruments, procedures, devices and techniques have been employed to perform the operation over the years. In general, these various procedures and techniques have attempted to achieve the goal of removing the excess foreskin from the glans penis with a minimum of trauma, pain, loss of blood and discomfort to the patient. Applicant's invention achieves these goals, removing the excess foreskin from the penis in a less painful and traumatizing manner. Through the use of a procedure and device which is an improvement over the devices, procedures and techniques known and used in the prior art.

The device and procedure utilized for performing circumcisions in accordance with the instant invention has a great advantage over prior art devices and procedures. One particular advantage of applicant's invention over the prior art is the fact that prior art devices are generally made of metal or solid plastic.

In practice, the use of these solid materials results in a disadvantage because they require one or more postoperative visits to the doctor or the hospital to remove the device and to examine the patient to ensure that the circumcised penis has not become infected.

On the contrary, because the device of this invention is made of polygcolic acid, a material which is well known and used in medical circles as an absorbable suture, the need for post operative care is minimized. Because polygcolic acid can be absorbed into the human body systems, the need for postoperative care to remove sutures from the recently circumcised penis is eliminated, consequently, the patient does not have to make a special visit to the physician or nurse to remove the device from the penis or to apply dressing to the penis post-operatively.

Further, the device of this invention has an added advantage over prior art devices because it is simple and easy to use even by doctors having minimal training and experience in surgical procedures. Through the use of the device, and the related procedure, it is now possible to perform circumcisions without the need for lengthy hospitalization, complicated instrumentation or numerous specially trained personnel. Additionally, the invention has the advantage over the prior circumcision devices and procedures in that the device is made of materials which are cheap, readily available and well known.

SUMMARY OF THE INVENTION

The primary object of this invention is to provide a circumcision device comprising a pair of separate but interlockable rings which are used to hold the foreskin of the penis tightly in place so that the excess foreskin can be surgically removed during circumcision.

Another object of this invention is to provide a pair of circumcision rings which can be made in varying sizes and various anatomical shapes in accordance with the needs of the patient.

A further object of the invention is to provide a pair of interlockable rings for use as a circumcision device which are composed of an absorbable substance so that the rings are left in place after the end of the operation and are absorbed naturally into the body thereby minimizing the need for post-operative care.

A still further object of the invention is to provide a device which is made of known material and which is simple to use and easily manufactured.

Yet another object of this invention is to provide a procedure for performing circumcisions by ligation which is quick and easy to carry out, requires a minimum stay in the hospital and which can be preformed without specially trained personnel in the process.

Accordingly, it is a object of the present invention to provide a novel circumcision device comprising an uninterrupted or solid inner ring adapted to be engaged under the foreskin of the penis, and a concentric, grooved outer ring which is interlockable with the inner ring so that the inner ring fits into and can be clamped into the body of the outer ring. In addition to the two rings, the device of the invention also includes a cylindrical carrier which is used for the purpose of placing the rings over the penis during circumcision.

In accordance with the invention, there is a first outer ring which is grooved in a channel-like manner around the entire angular circumference of the ring. The opening or mouth of the groove is partially covered by means of a lip, a flexible extension of the circumference, which extends from one side of the mouth of the groove partially across the opening into the groove. The lip on the outer ring serves a dual function. First, because it only covers the opening into the groove in the outer ring partially, it facilitates the process of holding the inner ring and the foreskin of the penis within the groove on the outer ring.

The invention also includes a second ring, having a solid circumference, this ring has one face slightly flattened so that the portion of the ring which comprises the circumference is not completely circular. The material used in the manufacture of the rings is polyglycolic acid, a flexible material which makes it quite easy to lock the solid ring in place in the groove or channel of the outer ring.

In addition, the invention includes a hollow tubular device which functions as a means of bringing the inner and outer rings together on the penis.

In practice, the outer ring of the device is placed onto the shaft of the penis and the inner ring is placed on the body of the hollow tubular cylindrical carrier. The front end of the carrier is hollow so that the frontal portion of the penis can be inserted into the opening in the cylindrical carrier. With the outer ring on the stem of the carrier, the frontal portion of the penis is placed inside the end of the cylindrical carrier and the foreskin of the penis is stretched over the front portion of the carrier. The carrier is pushed forward under the foreskin until the foreskin is turned inside out at the point which the foreskin and penis are connected to each other. The outer ring is trapped under the foreskin on the shaft of the penis, the solid inner ring is moved from its position on the body of the carrier and locked into the groove in the outer ring.

The positioning of the inner ring and the foreskin into the grooved outer ring causes the foreskin to be pulled taut and locked into place in the groove in the outer ring. The inner ring and the lip which partially covers the opening into the grooved outer ring act as retainers to keep the foreskin taut and in place so that the surgeon will be able to make a clean incision to remove the excess foreskin from around the penis.

Removal of the excess foreskin and the dressing of the wound completes the surgical procedure of circumcision in accordance with this invention. Thereafter, the patient can quickly be released from the hospital without the necessity of extended post operative care. The quick release from the hospital is facilitated by the fact that both the grooved outer ring and the solid inner ring are made of polyglycolic acid, an absorbable material, which when left in place on the penis disintegrates and is absorbed into the body. Thus, follow-up visitations with the surgeon may not be necessary or are minimized.

BRIEF DESCRIPTION OF THE DRAWINGS

Referring now to the drawings.

FIG. 1A is a drawing of the inner ring showing a cross-sectional view through the wall of the device.

FIG. 1B is a cross-sectional view of the solid wall of the inner ring of the device.

DETAILED DESCRIPTION

Figure 4:
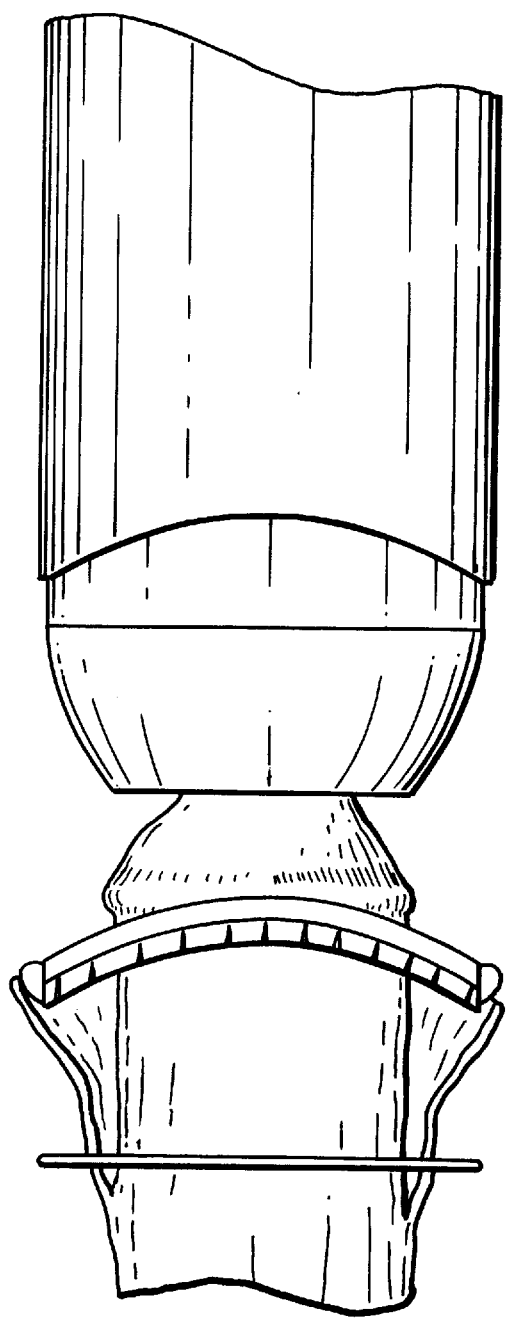
FIG. 4 shows the inner and outer rings and the carrier device positioned on the penis prior to the foreskin being folded over for insection with the inner ring into the groove of the outer ring.

Referring to the drawings, and particularly to FIG. 4, thereof, the preferred embodiment of the invention includes inner and outer polyglycolic acid rings 10 and 11 respectively which are separated from each other but are constructed so that the inner ring 10 can be locked into a groove or channel in the outer ring 11 to facilitate the successful performance of the invention.

Figure 2B:
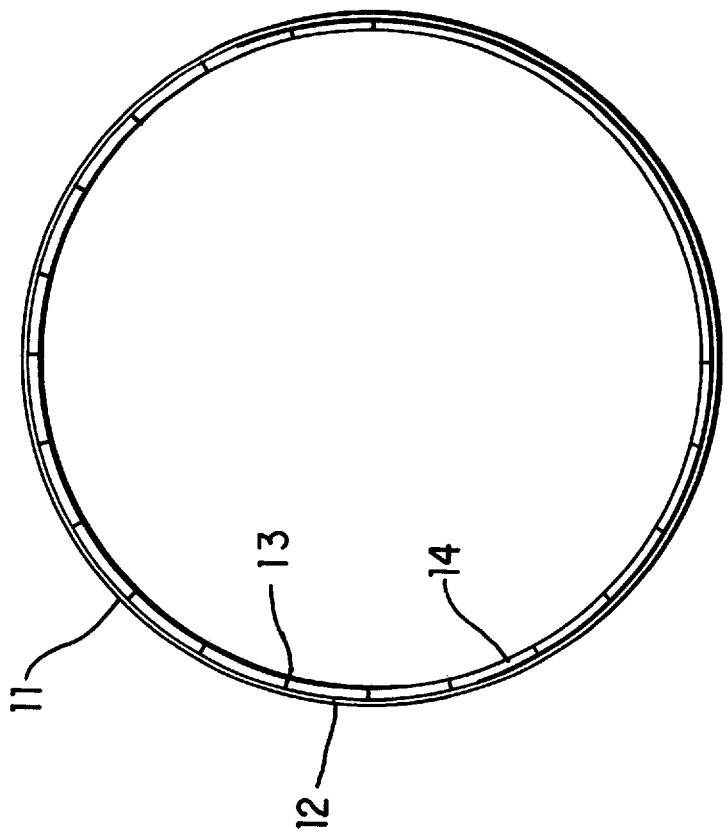
FIG. 2B is a drawing of the outer ring of the device.
Figure 2A:
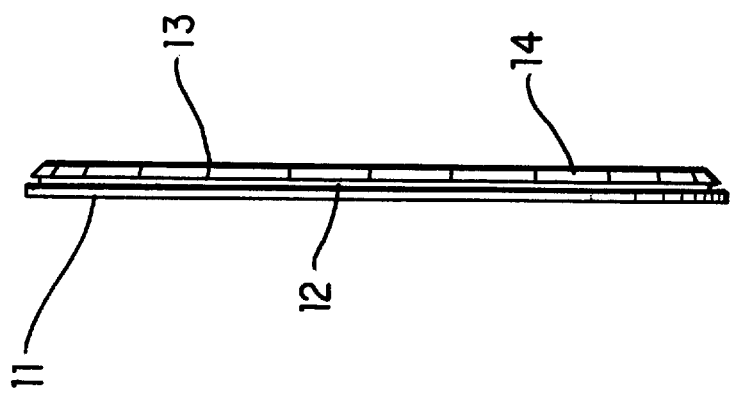
FIG. 2A is a vertical cross-section through the wall of the outer ring showing three sections; a solid outside wall section; an inside section which is slit at regular intervals to create the openings for insertion of the inner ring and a vacant middle which represents the groove in the circumferential wall of the outer inner ring.
Figure 3:
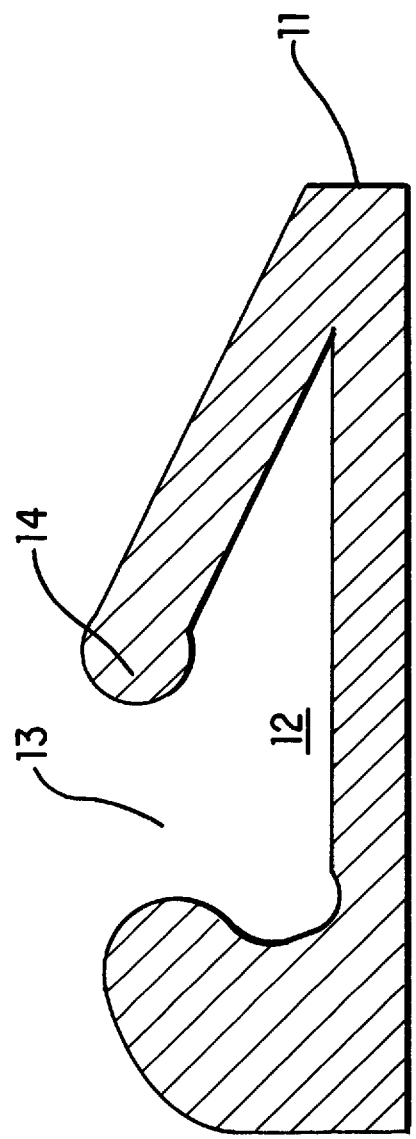
FIG. 3 is an enlarged vertical cross-section of the wall of the outer ring showing the groove within the wall of the ring, including the groove 12, opening into groove 13 and lip 14.

As shown in FIG. 1, the inner ring 10 is solid along its entire circumferential surface. On the other hand, the outer ring 11 contains a deep semi-covered channel like opening all along the circumferential surface as shown in FIGS. 2 and 3. In accordance with FIG. 3, at its narrowest point, the cross sectional diameter of the channeled section of the outer ring has a cross-sectional diameter of approximately 2.2 mm, the channel is approximately 1.2 mm deep. The mouth of the channel which is covered by a flexible liplike protrusion 14 is approximately 1 mm wide to facilitate the placement of the foreskin 15 and the inner ring 10 into a locking position within the channel of the outer ring.

With the foreskin being tightly stretched, held and locked into place in the channel of the outer ring, the surgeon is able to determine the point at which to make a clean incision to remove the excess foreskin 15. Because the foreskin is held tightly in place, the flow of blood is lessened in the region of the foreskin to be excised and the procedure can be completed with minimum loss of blood.

FIG. 4 illustrates the manner in which the invention is used. First, the solid inner ring 10 is placed over the shaft of penis 16, and the outer ring is over the hollow tubular instrument, then the hollow tubular instrument with the second outer ring is placed over the front end of the glans penis but under the foreskin, i.e. the foreskin is separated from the front end of the penis and is streched over the end of the hollow tubular instrument. When the front end of the hollow tubular instrument cannot be advanced further over the front end of the penis, that is when the hollow tubular instrument reaches the position at which the foreskin and the body of the penis are attached to each other, the foreskin of the penis is folded backwards onto the shaft of the penis so that the outer grooved ring is located under the foreskin on the shaft of the penis at or near the position at which the foreskin is attached to the shaft of the penis. The inner ring is then moved from its position on the hollow tubular instrument and placed over the foreskin, and the ring and foreskin inserted and locked into the channel like opening in the body of the outer ring. At this point, all that remains to be done to complete the circumcision procedure in accordance with the invention is to have the surgeon remove the foreskin surgically by making an incision on the foreskin nearwards of the point at which the inner ring and foreskin are inserted into the outer ring.

While the instant invention has been shown and described herein in its preferred embodiment, it is recognized that departures may be made therefore within the scope of the invention, which is therefore not limited to the details disclosed herein.

I claim:

1. A circumcision device for removing foreskin from the penis comprising a pair of unbroken, interlockable, concentric rings, including an inner ring and an outer ring and wherein said inner ring has a solid continuous annular surface and wherein said outer ring is generally C-shaped and has a channel within the circumferential wall of said ring and wherein said circumferential wall of said outer ring includes a flexible member for locking and retaining said inner ring and said foreskin of said penis within said channel in said circumferential wall of said outer ring and wherein each pair of said rings is constructed and sized so that said inner ring fits into and is lockable into said channel in said circumferential wall of said outer ring to form said circumcision device and wherein placement of said inner ring and said foreskin into said channel within said circumferential wall of said outer ring is the means of retaining said foreskin within said channel between said inner and outer rings to facilitate the surgical removal of said foreskin from said penis.

2. A circumcision device as defined in claim 1, wherein said inner and outer rings are designed so that said inner ring fits into said channel in said circumferential wall of said outer ring, so that when said inner and outer rings and said foreskin of said penis are locked into place inside said circumferential wall of said outer ring said pair of rings complement each other to form a single circumcision device.

3. A circumcision device as defined in claim 1, wherein each pair of said concentric rings is constructed so that the outside diameter of said inner ring and the inside diameter of said circumferential wall of said outer ring are approximately equal in diameter so that when said inner ring is inserted into said outer ring, said inner ring fits tightly into said circumferential wall of said outer ring to facilitate the locking and retention of the said solid inner ring and said foreskin of said penis into said channel in said outer ring to facilitate the removal of said foreskin from said penis.

4. A circumcision device as defined in claim 1, wherein said inner and outer rings are made of polyglycolic acid, or any other suitable bio-compatible material.

5. A circumcision device as defined in claim 1, wherein the inner ring has a solid, circular, uninterrupted, unitary, molded structure and is made of polyglycolic acid or any other flexible bio-compatible material.

6. A circumcision device comprising an inner ring member adapted to be positioned between the foreskin and the shaft of a penis during circumcision and an outer ring member adapted to be positioned on the outside of the shaft of said penis and said outer member being capable of accommodating and holding said foreskin and said inner ring member simultaneously in a channel within said inside surface of said outer ring member, said inner ring member and said foreskin being inserted into said outer ring member by pressing said foreskin and said inner member into said channel within said outer ring member so as to hold said foreskin tightly between said inner ring member and said outer ring member to facilitate the removal of said foreskin from said penis by surgical means.

7. A circumcision device as claimed in claim 1 wherein said inner and outer rings for use in performing the surgical procedure of the invention are made of a bio-compatible material to facilitate post-operative disintegration and absorption of said rings into the body so as to minimize the need for post-operative hospital and doctor visits and to minimize the cost of the operation.

8. A circumcision device as defined in claim 1, wherein said outer ring has a generally partially enclosed C-shaped channel within said circumferential wall of said outer ring and wherein the opening to said C-shaped channel is partially closed by an extension of said circumferential wall of said outer ring so that when said inner ring and said foreskin to be removed from said penis are enclosed within said circumferential wall of said outer ring, said inner ring and said foreskin to be removed from said penis are kept in place within said circumferential wall of said outer ring by means of said extension of said circumferential wall and wherein said circumferential wall is an unbroken, circular, unitary, molded structure made from polyglycolic acid or any other suitable bio-compatible material.

9. A circumcision device as defined in claim 6 wherein said inner and outer rings are made of polyglycolic acid, or any other suitable bio-compatible material.

10. A circumcision device as defined in claim 6, wherein said inner ring has a solid, circular, uninterrupted, unitary, molded structure and is made of polyglycolic acid or any other flexible bio-compatible material.

11. A circumcision device as defined in claim 6 wherein the opening into said outer ring member is constructed so that when said inner rind member and said foreskin are pressed into said outer ring member said inner ring member and said foreskin are held firmly in place inside said outer ring member and wherein the opening into said outer ring member is flexible enough to facilitate the pressing of said inner ring member and said foreskin into said outer ring member but firm enough to retain said inner ring member and said foreskin in place within said outer ring member.

12. A circumcision device as defined in claim 6 wherein each pair of said ring members is constructed so that the outside diameter of said inner ring member and the inside diameter of said outer ring member are approximately equal in diameter.

13. A circumcision device as defined in claim 6 wherein the opening to said channel within said inside surface of said outer ring is narrower than the circumference of said inner ring member.

\* \* \* \* \*